United States Patent
Alferiev et al.

(10) Patent No.: US 6,890,998 B2
(45) Date of Patent: *May 10, 2005

(54) THIOL ACTIVATION OF POLYURETHANES AND METHODS OF MAKING THE SAME

(75) Inventors: Ivan Alferiev, Clementon, NJ (US); Ilia Fishbein, Philadelphia, PA (US); Robert J. Levy, Merion Station, PA (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/672,893

(22) Filed: Sep. 26, 2003

(65) Prior Publication Data

US 2004/0102598 A1 May 27, 2004

Related U.S. Application Data (60) Provisional application No. 60/413,460, filed on Sep. 26, 2002.

(51) Int. Cl.$^7$ .............................................. C08G 18/82
(52) U.S. Cl. ........................ 525/452; 525/453; 525/454
(58) Field of Search ................ 525/452, 453, 525/454

(56) References Cited

U.S. PATENT DOCUMENTS

| | | |
|---|---|---|
| 4,521,564 A | 6/1985 | Solomon et al. |
| 5,073,575 A | 12/1991 | Blanch et al. |
| 5,134,035 A | 7/1992 | Kumar et al. |
| 6,320,011 B1 | 11/2001 | Levy et al. |
| 2004/0063158 A1 | 4/2004 | Alferiev et al. |
| 2004/0092698 A1 | 5/2004 | Alferiev et al. |

OTHER PUBLICATIONS

Phaneuf, M.D. et al., "Covalent Linkage of Recombinant Hirudin to a Novel Ionic Poly (Carbonate) Urethane Polymer with Protein Binding Sites: Determination of Surface Antithrombin Activity", Artif. Organs 1998; 22:657–65.

Huang L.L.H. et al., "Comparison of Epoxides on Grafting Collagen to Polyurethane and Their Effects on Cellular Growth", J. Biomed. Mater. Res. 1998; 39:630–6.

Lincoff et al., J.Am. Coll. Cardiol., 29, 808.16 (1997).

*Primary Examiner*—Rachel Gorr
(74) *Attorney, Agent, or Firm*—Caesar, Rivise, Bernstein, Cohen & Pokotilow, Ltd.

(57) ABSTRACT

A polyurethane having a thiol substituent pendant from at least one nitrogen and/or at least one carbon atom of the polyurethane.

A polyurethane having a thiol substituent pendant from at least one nitrogen and/or at least one carbon atom of the polyurethane, wherein the thiol substituent has a formula:

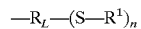

$$-R_L-(S-R^1)_n$$

wherein n is an integer from 1 to 3; $R_L$ is an (n+1)-valent organic radical having at least one carbon atom; and $R^1$ is a member selected from the group consisting of H, C(O)$R^3$, and S$R^4$, wherein $R^3$ is a member selected from the group consisting of $C_1$ to $C_6$ alkyl and $R^4$ is a heterocyclic group or an electron deficient aromatic group.

47 Claims, 4 Drawing Sheets

A = p-$C_6H_4CH_2C_6H_4$-p (polyurethanes based on MDI) or
cyclo-$C_6H_{10}CH_2C_6H_{10}$-cyclo (aliphatic polyurethanes based on HMDI)
X = residue of polytetramethyleneoxide (polyether-urethanes) or
polycarbonatediol (polycarbonate-urethanes)

THIOL ACTIVATION OF POLYURETHANES AND METHODS OF MAKING THE SAME

CROSS-REFERENCE TO RELATED APPLICATIONS

This application claims benefit of provisional Application No. 60/413,460, filed Sep. 26, 2002, which is incorporated herein in its entirety.

STATEMENT REGARDING FEDERALLY SPONSORED RESEARCH OR DEVELOPMENT

This research was supported by U.S. Government funds (National Heart, Lung and Blood Institute grant number NHLBI 59730), and the U.S. Government may therefore have certain rights in the invention.

BACKGROUND OF THE INVENTION

1. Field of Invention

This invention relates generally to the field of derivatized polyurethane polymers for in vitro and in vivo use.

2. Description of Related Art

Polyurethanes are polymers, which can be made by condensing a diisocyanate with a diol, with two or more diols having different structures, or with a diol and a diamine.

Medical grade segmented polyurethanes are usually prepared by condensing a diisocyanate with a polymeric diol having a molecular weight of about 1,000 to 3,000 (e.g., polytetramethyleneoxide for polyether-urethanes or polycarbonatediols for polycarbonate-urethanes) in order to form a polyurethane precursor which is subsequently reacted with an approximately equivalent amount of a chain extender (e.g., a diol such as 1,4-butanediol or a diamine such as a mixture of diaminocyclohexane isomers).

Polyurethanes can be used to form bulk polymers, coatings, fillings, and films. Once set, polyurethanes are also readily machinable. Polyurethanes were used for medical and non-medical purposes since at least the beginning of the twentieth century.

One type of medical application of polyurethanes involves a covalent immobilization of various proteins, cells, antibodies, and/or enzymes onto a polyurethane surface to make modified polyurethanes. Such modified polyurethanes would be useful in tissue engineering and artificial organ concepts, wound dressings, and gene delivery systems by making virtually any surgical implant and interventional device potentially therapeutic.

Surface coatings and treatments, however, are problematic in that they can invoke acute or chronic inflammatory responses to the coatings themselves. The use of synthetic polymers and biopolymer coatings for delivery purposes can, in some instances, result in an undesirable hyperproliferation response among cells that contact the polymeric material. Polyurethane, poly(dimethyl siloxane) and polyethylene terephthalate coated stents are known to cause inflammation and thrombus formation. Low molecular weight poly-L-lactic acid coatings also cause an inflammatory response. Lincoff et al., *J. Am. Coll. Cardiol.*, 29, 808.16 (1997).

Prior art polyurethanes that are suitably modified for the covalent immobilization of various proteins are rather limited in number and utility. For example, polyurethanes containing pendant carboxy groups were synthesized in order to covalently attach recombinant hirudin (Phaneuff, M. D. et al. "Covalent Linkage of Recombinant Hirudin to a Novel ionic Poly(carbonate)urethane Polymer With Protein Binding Sites: Determination of Surface Antithrombin Activity," *Artif Organs* 1998; 22:657–65). Alternatively, polyurethanes with pendant epoxy groups have been used for the covalent immobilization of collagen (Huang L. L. H. et al. "Comparison of Epoxides on Grafting Collagen to Polyurethane and Their Effects on Cellular Growth," *J. Biomed. Mater. Res.* 1998; 39:630–6).

One example of derivatizing polyurethanes with reactive moieties so such polyurethanes can react with molecules of interest, for example, bioactive molecules is polyurethane derivatized to contain pending geminal bisphosphonate groups disclosed in U.S. Pat. No. 6,320,011 to Levy et al. Derivatized polyurethane can then react with proteins, cells, antibodies, and/or enzymes.

Polyurethanes that are similarly modified with pendant thiol groups would be highly desirable and of more general utility than prior art polyurethanes. For example, polyurethanes having pendant thiol functionalities would be widely applicable for the conjugation of biologically active molecules such as proteins and would be very reactive in physiological environments. A significant challenge in preparing macromolecules that contain multiple thiol groups, however, lies in the unavoidable oxidative cross-linking of such macromolecules and subsequent reduction or loss of certain characteristics such as flexibility.

Therefore, despite there is a need for polyurethanes containing pendant thiol groups, which can be employed in a vast array of thiol-mediated biochemical interactions. Additionally, a need exists for methods of making such polyurethanes, which methods circumvent oxidative cross-linking of polymer molecules.

All references cited herein are incorporated herein by reference in their entireties.

BRIEF SUMMARY OF THE INVENTION

Accordingly, the invention provides a polyurethane comprising a thiol substituent pendant from at least one nitrogen and/or at least one carbon atom of the polyurethane.

In certain embodiments, the thiol substituent has a formula:

$$—R_L—(S—R^1)_n$$

wherein n is an integer from 1 to 3; $R_L$ is an (n+1)-valent organic radical comprising at least one carbon atom; and $R^1$ is a member selected from the group consisting of H, $C(O)R^3$, and $SR^4$, wherein $R^3$ is a member selected from the group consisting of $C_1$ to $C_6$ alkyl and $R^4$ is a heterocyclic group or an electron deficient aromatic group.

In certain embodiments, $R_L$ is a bivalent organic radical selected from the group consisting of $C_1$ to $C_{18}$ alkylene, $C_1$ to $C_{18}$ alkyleneamino, $C_1$ to $C_{18}$ alkyleneoxy, $C_1$ to $C_{18}$ haloalkylene, $C_2$ to $C_{18}$ alkenylene, $C_6$ to $C_{18}$ arylene, a modified $C_2$ to $C_{18}$ alkenylene having at least one carbon substituted by a halogen group, $C_2$ to $C_{18}$ alkenylene having one or more O, S, or N atoms incorporated into an alkenylene chain, a bivalent heterocyclic radical, and mixtures thereof. Preferably, $R_L$ is $C_1$ to $C_6$ alkylene and most preferably, $R_L$ is butylene.

In certain embodiments, the bivalent heterocyclic radical is a member selected from the group consisting of thiazoline, thiazolidone, imidazol, imidazoline, thiazole, tetrazole, thiadiazole, imidazole, pyridine, and morpholine. Preferably, the bivalent heterocyclic radical is pyridine.

In certain embodiments, $R^1$ is H and/or $SR^4$.

The polyurethane of claim 2, wherein $R^4$ is 2-pyridyl and/or 3-carboxy-4-nitrophenyl.

In certain embodiments, the thiol substituent is pendant from about 0.5 to 50% of urethane nitrogen atoms. In certain embodiments, the thiol substituent is pendant from about 0.5 to about 50% of carbon atoms. Preferably, the thiol substituent is pendant from 1 to 20% of urethane nitrogen and/or carbon atoms, and most preferably, the thiol substituent is pendant from 5 to 10% of urethane nitrogen and/or carbon atoms.

In certain embodiments, the polyurethane comprises at least about 10 micromoles of the thiol substituent per gram of the polyurethane.

In certain embodiments, the polyurethane has at least two different thiol substituents pendant from urethane nitrogen and/or carbon atoms.

In certain embodiments, the thiol substituent is an acetylthio group.

In certain embodiments, the thiol substituent is a 3-carboxy-4-nitrophenyldithio group.

Also provided is a process for preparing the polyurethane of the invention, the process comprising:
providing a polyurethane comprising a urethane amino moiety;
providing a multifunctional linker reagent of a formula:

wherein n is an integer from 1 to 3, FG is a functional group selected from the group consisting of a halogen, a carboxyl group, a sulfonate ester, and an epoxy group, LG is a leaving group selected from the group consisting of a halogen, a carboxyl group, a sulfonate ester, and an epoxy group, and $R_L$ is an (n+1)-valent organic radical comprising at least one carbon atom;
providing a protected thiol-containing reagent of a formula R—C(O)SH, or a salt thereof, wherein R is a $C_1$ to $C_6$ alkyl group;
reacting the multifunctional linker reagent with the urethane amino moiety to form a polyurethane substituted with at least one substituent group of a formula reacting the polyurethane substituted with at least one substituent group with a protected thiol-containing reagent to form the polyurethane comprising the thiol substituent pendant from the at least one nitrogen and/or the at least one carbon atom.

In certain embodiments of the process of the invention, $R_L$ is a bivalent organic radical selected from the group consisting of $C_1$ to $C_{18}$ alkylene, $C_1$ to $C_{18}$ alkyleneamino, $C_1$ to $C_{18}$ alkyleneoxy, $C_1$ to $C_{18}$ haloalkylene, $C_2$ to $C_{18}$ alkenylene, $C_6$ to $C_{18}$ arylene, a modified $C_2$ to $C_{18}$ alkenylene having at least one carbon substituted by a halogen group, $C_2$ to $C_{18}$ alkenylene having one or more O, S, or N atoms incorporated into an alkenylene chain, a bivalent heterocyclic radical, and mixtures thereof.

In certain embodiments of the process of the invention, $R_L$ is a member selected from the group consisting of $C_1$ to $C_6$ alkylene.

In certain embodiments of the process of the invention, $R_L$ is butylene, FG is a bromo group, LG is a bromo group and n is 1.

In certain embodiments of the process of the invention, LG is a bromo group.

In certain embodiments of the process of the invention, the sulfonate ester is a member selected from the group consisting of mesylate, triflate, and tosylate.

In certain embodiments of the process of the invention, the sulfonate ester is a member selected from the group consisting of a ω-bromoalkyl mesylate, a ω-bromoalkyl triflate, and a ω-bromoalkyl tosylate.

In certain embodiments of the process of the invention, the multifunctional linker reagent is a member selected from the group consisting of a dibromoalkyl compound, a bromo-carboxyalkyl compound, and a bromo-epoxyalkyl compound.

In certain embodiments of the process of the invention, the dibromoalkyl compound is a 1,ω-dibromoalkyl compound or a substituted 1,ω-dibromoalkyl compound.

In certain embodiments of the process of the invention, the dibromoalkyl compound is a $C_2$–$C_6$ 1,ω-dibromoalkyl compound.

In certain embodiments of the process of the invention, the dibromoalkyl compound is 1,6-dibromohexane or 1,4-dibromobutane.

In certain embodiments of the process of the invention, the bromo-carboxyalkyl compound is a ω-bromocarboxylic acid or a substituted ω-bromocarboxylic acid.

In certain embodiments of the process of the invention, the bromo-epoxyalkyl compound is epibromohydrin.

In certain embodiments of the process of the invention, the process is conducted in a presence of an aprotic solvent.

In certain embodiments, the aprotic solvent is a member selected from the group consisting of N,N-dimethylacetamide, N,N-dimethyl formamide, 1-methyl-2-pyrrolidinone, tetrahydrofuran, dioxane, and dimethyl sulfoxide.

Preferably, the process is conducted in a presence of a base soluble in the aprotic solvent.

In certain embodiments of the process of the invention, the base is a member selected from the group consisting of sodium hydride, lithium diisopropylamide, and sodium.

In certain embodiments of the process of the invention, the base is potassium tert-butoxide, dimsyl sodium, lithium hydride, sodium amide, lithium N,N-dialkylamide, or lithium N,N-dicyclohexylamide. In certain embodiments, the base is lithium tert-butoxide.

In certain embodiments of the process of the invention, the multifunctional linker reagent is 1,6-dibromohexane, and the base is lithium diisopropylamide.

In certain embodiments of the process of the invention, the multifunctional linker reagent is 1,4-dibromobutane.

In certain embodiments of the process of the invention, the protected thiol-containing reagent is thiolacetic acid.

In certain embodiments of the process of the invention, the protected thiol-containing reagent is tetrabutylammonium thioacetate.

In certain embodiments of the process of the invention, the protected thiol group with a deprotecting reagent to remove an R—C(O)— fragment from the thiol substituent to obtain the polyurethane.

In certain embodiments of the process of the invention, the deprotecting reagent is a member selected from the group consisting of ammonia, primary aliphatic amines, aqueous solutions of alkali metal hydroxides, carbonates, tri-substituted phosphates, hydroxylamine, and hydrazine.

Further provided is a process of producing a molded product, said process comprising:
providing the polyurethane of claim 1, wherein the thiol substituent is protected;
molding the polyurethane to form an article; and
deprotecting the thiol substituent of the article to provide the molded product.

In certain embodiments, the process of producing a molded product further comprises reacting the thiol substituent of the molded product with a biomolecule.

Also provided is a molded product produced by the process of the invention.

BRIEF DESCRIPTION OF SEVERAL VIEWS OF THE DRAWINGS

The invention will be described in conjunction with the following drawings in which like reference numerals designate like elements and wherein:

FIG. 2 shows a reaction sequence by which a quantitative assay of surface thiol-reactive groups is carried out. Polyurethane 3 is treated with the deprotecting reagent hydroxylamine ($NH_2OH$) to give polyurethane 4 having pendant thiol groups. The wavy lines represent $R_L$, an organic radical comprising at least one carbon atom. The thiol groups are then tagged with a fluorescent moiety by treating them sequentially with 5,5'-dithiobis(2-nitrobenzoic acid) ("DTNB") and the thiol-containing fluorophore dansyl-L-cysteine ("Fl-SH"). The resultant polyurethane 6 comprises fluorescent moieites ("Fl") attached to the polyurethane via disulfide bonds. Reduction of the disulfide bonds by tris(carboxyethyl)phosphine ("TCEP") regenerates polyurethane 4 and liberates dansyl-L-cysteine (Fl-SH) into solution.

thiol substituent pendant from at least one nitrogen and/or at least one carbon atom of the polyurethane.

DETAILED DESCRIPTION OF THE INVENTION

The present invention is based upon the discovery of polyurethanes that have thiol substituents pendant from at least one nitrogen and/or at least one carbon atom of the polyurethane and methods of making such polyurethanes. An advantage of this invention is that the methods are efficacious under relatively mild conditions, which decrease the potential for polyurethane decomposition. Yet another advantage is that the polyurethanes are sufficiently robust to withstand conditions that are typical for high temperature processing of polyurethanes, and thus avoid the oxidative thiol cross-coupling that attends other macromolecules containing multiple thiol groups. Accordingly, the present polyurethanes can be molded or extruded for use in many applications, including therapeutic implants and interventional devices. In this context, the present invention provides the use of sulfhydryl chemistry for immobilizing proteins, cells, and other complex constructs, such as gene delivery systems, on the surface of medical grade polyurethanes.

Polyurethanes

In accordance with the teachings of this invention, the polyurethane has at least one pendant thiol substituent which is either thiol or protected thiol group or a mixture of both.

The term "polyurethane," as used herein, is a polymer that comprises repeating units having a urethane group in the polymer backbone. Such polymers include, for example, polyurethane homopolymers, block co-polymers comprising at least one polyurethane block, and polymer blends comprising such homopolymers and block co-polymers. Illustrative polyurethanes include but are not limited to F2000 PEU, which is a medical grade polyether-urethane prepared from 4,4-methylenebis(phenylisocyanate), polytetramethyleneoxide (MW ca. 1,000 g/mol), and 1,4-butanediol as a chain extender (Sulzer Carbomedics, Inc.; Austin, Tex.); BIO-SPAN™, which is a medical grade polyurethane-urea and BIONATE™ 80A, which is a medical grade polycarbonate-urethane (both from Polymer Technology Group Medical, LLC; Berkeley, Calif.); and TECO-THANE™ TT-1074A, which is a medical grade polyether-urethane (Thermedics, Inc.; Woburn, Mass.).

A chemical substituent is "pendant" from a backbone of a polymer if it is bound to an atom of a monomeric unit of the polymer. In this context, the substituent can be pending from a carbon atom of a backbone, a carbon atom connected to a carbon atom of the backbone by a chain extender, or a urethane nitrogen of the backbone of the polyurethane.

In one embodiment of the invention, the thiol or protected thiol substituent is pendant from a urethane nitrogen of the backbone of the polyurethane. As used herein, a "urethane" refers to a chemical subunit of a polyurethane backbone and that has the following general structure:

wherein the wavy lines signify bonds to the rest of the polyurethane backbone.

As mentioned above, the thiol or protected thiol groups have a general formula $—R_L—(S—R^1)_n$, wherein $R_L$ is a multivalent organic radical. The chemical identity of $R_L$ is not critical, except that it must comprise at least one carbon atom. Since "n" can vary between 1 and 3, $R_L$ may carry 1, 2, or 3 $S—R^1$ moieties, respectively, thus providing polyurethanes with mixed thiol or protected thiol substituents. Preferably, "n" is 1, where $R_L$ serves as a bivalent organic radical.

Bivalent organic radicals suitable as $R_L$ include, for example, straight or branched $C_1$ to $C_{18}$ alkylene groups. Illustrative alkylene groups are methylene, ethylene, propylene, butylene, pentylene, and hexylene. Preferably, $R_L$ is butylene. The alkylene groups may be substituted by one or more halo substituents, which include —F, —Cl, —Br, and —I.

Other bivalent organic radicals include $C_1$ to $C_{18}$ alkyleneamino and $C_1$ to $C_{18}$ alkyleneoxy groups. Alkyleneamino groups are alkylene groups that are interrupted by one or more amino fragments. Similarly, $C_1$ to $C_{18}$ alkyleneoxy groups are alkylene groups that are interrupted by one or more oxy (i.e., —O—) moieties.

Still other bivalent organic radicals are cyclic moieties such as arylene groups and bivalent heterocyclic radicals. An arylene group is a $C_6$ to $C_{12}$ bivalent aromatic hydrocarbon. Exemplary arylene groups are phenylene and napthylenylene. Bivalent heterocyclic radicals are preferably 5- to 6-member heterocycles containing at least one heteroatom selected from N, S, and O, such that two valences on the heterocycle are available for forming bonds. Exemplary heterocycles include thiazoline, thiazolidone, imidazole, imidazoline, thiazole, triazoles, tetrazole, thiadiazole, imidazole, pyridine, and morpholine.

For polyurethanes that comprise protected thiol substituents, $R^1$ in the formula above can be an acyl group of the formula $C(O)R^3$. $R^3$ is a straight or branched $C_1$ to $C_6$ alkyl group. The most preferred $R^3$ is methyl. Alternatively, $R^1$ is of the formula $-SR^4$, wherein the polyurethane comprises pendant dithio groups. In this instance, $R^4$ is a heterocyclic group as defined above or an electron deficient aromatic group. Although any heterocycle would suffice, the preferred heterocycle is pyridine. The electron deficient aromatic group is defined as above for the arylene group, but which is also substituted with one or more electron-withdrawing substituents. Suitable substituents in this context include carboxyl, nitro, fluoro, chloro, bromo, formyl, esters, and sulfonate esters. The preferred electron deficient aromatic group is 3-carboxy-4-nitrophenyl.

The polyurethanes of this invention are further characterized in that about 0.5 to about 50% of the urethane nitrogen atoms of the backbone of the polyurethane carry a pendant thiol or protected thiol substituent. Preferably, about 1 to about 20%, and most preferably about 5 to about 10% of the nitrogen atoms carry such substituents.

Alternatively characterized, the polyurethane of the invention comprises at least about 10 micromoles of the thiol substituent per gram of the polyurethane.

In certain embodiments, the polyurethane of the invention comprise about 10 to about 400, preferably about 20 to about 200, micromoles of the thiol or protected thiol group per gram of polyurethane. As mentioned above, the polyurethane of this invention can comprise one type of such substituents, or it can comprise more than one type of substituents.

In another embodiment of the invention, the thiol or protected thiol substituent is pendant from a carbon atom of the polyurethane.

In yet another embodiment, the polyurethane of the invention comprises a plurality of thiol substituents pendant from at least one urethane nitrogen and at least one carbon atom of the polyurethane.

The polyurethanes of the invention are useful in the manufacture of a wide range of devices, including medical devices such as therapeutic implants and interventional devices. Implantable devices which can be made using the polyurethane of the invention include, but are not limited to, degradable and non-degradable sutures, orthopedic protheses such as supporting rod implants, joint protheses, pins for stabilizing fractures, bone cements and ceramics, tendon reconstruction implants, prosthetic implants, cardiovascular implants such as heart valve prostheses, pacemaker components, defibrillator components, angioplasty devices, intravascular stents, acute and in-dwelling catheters, ductus arteriosus closure devices, implants deliverable by cardiac catheters such as atrial and ventricular septal defect closure devices, urologic implants such as urinary catheters and stents, neurosurgical implants such as neurosurgical shunts, ophthalmologic implants such as lens prosthesis, thin ophthalmic sutures, and corneal implants, dental prostheses, and internal and external wound dressings such as bandages and hernia repair meshes.

An "implantable" device is one which is adapted for permanent or temporary insertion into or application against a tissue of an animal such as a human.

Process for Preparing Polyurethanes

The processes of this invention are implemented under mild conditions, such as low temperature, which allow the preparation of polyurethanes carrying pendant thiol groups. The processes thus circumvent any risk of oxidative cross-coupling between multiple thiol groups that would attend higher temperature synthetic routes.

One process of this invention provides the present polyurethane having at least one pendant thiol protected group. The process comprises first reacting the urethane amino moiety of a polyurethane with a multifunctional linker reagent of the general formula:

wherein $R_L$ and n are as described above and LG is a leaving group selected from the group consisting of a halogen, a carboxyl group, a sulfonate ester, and an epoxy group. Thus, the linker can be a bi-, tri-, tetra-functional linker. Preferred sulfonate esters include but are not limited to mesylate (i.e., $CH_3SO_2O-$), triflate (i.e., $CF_3SO_2O-$), and tosylate (i.e., $CH_3C_6H_4SO_2O-$). Preferred halogen group is a bromo group.

Reaction between polyurethane and the multifunctional linker reagent is also described in details in copending U.S. patent application entitled "DERIVATIZED POLYURETHANE COMPOSITIONS WHICH EXHIBIT ENHANCED STABILITY IN BIOLOGICAL SYSTEMS AND METHODS OF MAKING THE SAME," by Alferiev, Fishbein and Levy, filed on even date herewith and incorporated herein in its entirety.

The inventors have discovered that the bromine substituent of the multifunctional linker reagent is surprisingly reactive with polyanionic polyurethane, which is generated by maintaining polyurethane in the presence of a strong base. The reactivity is maintained at a temperature of less than about 30° C., less than about 20° C., less than about 10° C., less than about 0° C., and even less than about -5° C.

Each FG is a functional group that is independently selected from halo substituents such as chloro, bromo, and iodo; a carboxyl group; a sulfonate ester; and an epoxy group. The functional group is therefore a leaving group or is a group with which the protected thiol containing reagent described below forms a bond. Halo and sulfonate ester groups are (i.e., $CH_3SO_2O-$), triflate (i.e., $CF_3SO_2O-$), and tosylate (i.e., $CH_3C_6H_4SO_2O-$). When FG is a halo or sulfonate ester group, any carbon atom to which it can be attached is preferably an aliphatic carbon. When FG is an epoxy ring, however, any carbon to which it is attached can be aliphatic, unsaturated, or aromatic.

The multifunctional linker reagent can have various combinations of LG and FG groups and is not limited to the examples above. LG and one, two or three FG groups can be different or the same chemical group.

In a preferred embodiment of the method of the invention, the multi-functional linker reagent is a dibromoalkyl compound, a bromo-carboxyalkyl compound, or a bromo-epoxyalkyl compound. Particularly preferred dibromoalkyl compounds include 1,ω-dibromoalkyl compounds such as 1,6-dibromohexane, 1,4-dibromobutane, and substituted 1,ω-dibromoalkyl compounds. Particularly preferred bromo-carboxyalkyl compounds include ω-bromocarboxylic acids such as ω-bromohexanoic acid, ω-bromoundecanoic acid, and substituted ω-bromocarboxylic acids. Particularly preferred bromo-epoxyalkyl compounds include bromo-oxiranealkyl compounds such as epibromohydrin.

The inventors have discovered that dibromoalkyl compounds having relatively short alkyl chain lengths (e.g., dibromo-$C_2$, -$C_3$, -$C_4$, -$C_5$, and -$C_6$ compounds), and presumably bromo-carboxyalkyl and bromo-epoxyalkyl compounds having similarly short alkyl chain lengths, exhibit greater reactivity with urethane anionic moieties. Owing to this enhanced reactivity, a less strong base (e.g., lithium tert-butoxide) can be used, with the advantage that base-mediated degradation of the polyurethane can be reduced.

In another preferred embodiment, at least one functional group is a sulfonate ester. Thus, in this embodiment, the multi-functional linker reagent can, for example, be ω-bromoalkyl sulfonate esters such as ω-bromoalkyl mesylates (i.e., $CH_3SO_2O(CH_2)_qBr$, wherein q is an integer equal to or greater than 1), ω-bromoalkyl triflates (i.e., $CF_3SO_2O(CH_2)_qBr$), and ω-bromoalkyl tosylates.

The reaction described above is preferably performed in an aprotic solvent. The aprotic solvent can be substantially any aprotic solvent. An illustrative aprotic solvent is N,N-dimethylacetamide (DMAc), but a wide variety of other aprotic solvents can be used instead, including, for example, N,N-dimethyl formamide, 1-methyl-2-pyrrolidinone, tetrahydrofuran, dioxane, and dimethyl sulfoxide (DMSO).

Additionally, the reaction is best performed in the presence of a strong base, which renders the polyurethane amino nitrogen atoms into their more nucleophilic anionic forms. The strong base can be substantially any strong base that is soluble in the aprotic solvent used. Exemplary strong bases include sodium hydride, lithium diisopropylamide, sodium or potassium tert-butoxide, dimsyl sodium, lithium hydride, sodium amide, lithium N,N-dicyclohexylamide, and other lithium N,N-dialkylamides.

It is important to consider the effect that a counter-ion of the base may have upon the multi-functional linker, the derivatized polyurethane, or both. For example, the multi-functional linker should not be precipitated from solution, since this would complicate reaction of the linker with the polyurethane. Similarly, if it is desired that the derivatized polymer should remain in solution, a base should be chosen which does not have a counter-ion which would precipitate the derivatized polymer. For example, if the multi-functional linker comprises one or more carboxyl groups and several methylene groups, strong bases which have sodium counter-ions should be avoided. The same bases having lithium counter-ions, however, are preferable.

As noted above, when a multi-functional linker having a relatively high reactivity with polyurethane anionic moieties is used, the strength of the base can be lower than when a multi-functional linker having a lower reactivity is used. Thus, for example, strong bases such as lithium diisopropylamide (LDA) can be used when the linker is, for example, 1,6-dibromohexane, whereas relatively weaker bases such as lithium tert-butoxide are preferred when the linker is more reactive (e.g., 1,4-dibromobutane). Alternatively, lithium tert-butoxide can be used in combination with all multifunctional linker reagents. In this scenario, for example, the yield of bromoalkylation (i.e., the molar ratio of bromoalkylated urethane segments to base) exceeds 90% when lithium tert-butoxide is employed as compared to yields of 50–60% for LDA.

Continuing, the process further comprises reacting the polyurethane that is substituted with at least one —$R_L(FG)_n$ substituent with a protected thiol-containing reagent of the formula R—C(O)—SH or a salt thereof. Each R—C(O)—SH thus displaces one FG. Suitable reagents are those in which R is a $C_1$ to $C_6$ alkyl group. A particularly preferred reagent is thiolacetic acetic acid (i.e., $CH_3C(O)SH$).

The substitution of FG is preferably accomplished by using salts of R—C(O)—SH (i.e., [R—C(O)—S]X, where X is a cation), which are the most reactive toward —$R_L(FG)_n$ substituents. In principle, any salt may be used, such as those of sodium, potassium, or zinc, but in any case should be chosen such that the concentration of R—C(O)—$S^-$ in reaction mixtures is maintained at least at 0.1M, preferably 0.2 M. At these concentrations, complete substitution of functional groups FG can be realized. Thus, the most preferred salts are those containing cations that are relatively soluble in the solvent. For example, where the solvent is an aprotic solvent, as described above, the cation can be a tetralkyl ammonium ion such as $Bu_4N^+$ or $Me_4N^+$ and the like. Alternatively, the cation can be a protonated strong organic base, where the base is, for example, a strong tertiary amine such azabicyclooctane, guanidine or an N-alkyl derivative of guanidine, or tetramethyl-1,8-diaminonaphthalene. The most preferred salt is tetrabutylammonium thioacetate (i.e., $(Bu_4N)S(O)CCH_3$).

As mentioned above, the concentration of R—C(O)—$S^-$ should be maintained at least at 0.1 M. In one embodiment, this can be accomplished by adding the requisite amount of pre-formed R—C(O)—SX to a solution of the polyurethane having —$R_L(FG)_n$ substituents. Alternatively, the reaction between the polyurethane having —$R_L(FG)_n$ substituents and the protected thiol reagent is performed in the presence of a proton scavenger that is not susceptible to alkylation. One class of suitable scavengers includes tetralkalkyammonium salts of a weak acid. For example, the tetralkalkyammonium salt of a weak acid can be tetrabutylammonium borate, carbonate, hydrocarbonate, or hydroxide. Another class of suitable scavengers is neutral organic bases, such as sterically-hindered tertiary amines, N-alkylguanidines, and tetramethyl-1,8-diaminonaphthalene. Preferably, the substitution of FG is performed in the presence of R—C(O)—$S^-$, although such substitution can be achieved with mixtures of R—C(O)—SH and R—C(O)—$S^-$ (e.g., 1:1 molar ratio).

The polyurethane prepared by the process described above exhibits remarkable thermal stability. Thus, the polyurethane can be subjected to the high temperatures typically encountered in routine processing methods such as molding and extrusion that are used to form, for example, medical devices as described above. Because the polyurethane has pendant protected thiol groups, such processing can be performed without the risk of degradation that would otherwise result from oxidative cross-coupling of pendant thiol groups. Once the polyurethane is processed into a desired form, the thiol groups can be deprotected.

Accordingly, the present invention also provides a process of preparing a polyurethane having pendant thiol groups. The process comprises the two steps described above to furnish a polyurethane having pendant protected thiol groups. The polyurethane is then treated with a reagent that can deprotect the protected thiol groups, e.g., remove the R—C(O)— fragment via acid- or base-catalyzed hydrolysis. Suitable reagents in this context include ammonia; primary aliphatic amines; aqueous solutions of alkali metal hydroxides, carbonates, or trisubstituted phosphates; hydroxylamine; and hydrazine. A preferred deprotecting reagent is hydroxylamine (e.g., $NH_2OH$).

Further, the polyurethane of the invention can be prepared by using chain extenders comprising a leaving group (LG)

suitable for nucleophilic substitution instead of multilinker as described above.

Non-limiting examples of the leaving group are halogens, a carboxyl group, a sulfonate ester, and an epoxy group. In certain embodiments, sulfonate ester is selected from the group consisting of mesylate, triflate, and tosylate. Among halogens, a bromo group is preferred.

Chain extenders contemplated in the invention are of a kind known in the art. The chain extenders comprising an alkyl chain, at least one hydroxy group, and a leaving group as defined above are preferred.

In the method, polyurethane precursors terminated with isocyanate groups are used. In certain embodiments, polyurethane precursors are based on methylene diphenyl diisocyanate (MDI) or HMDI.

Figure 1:
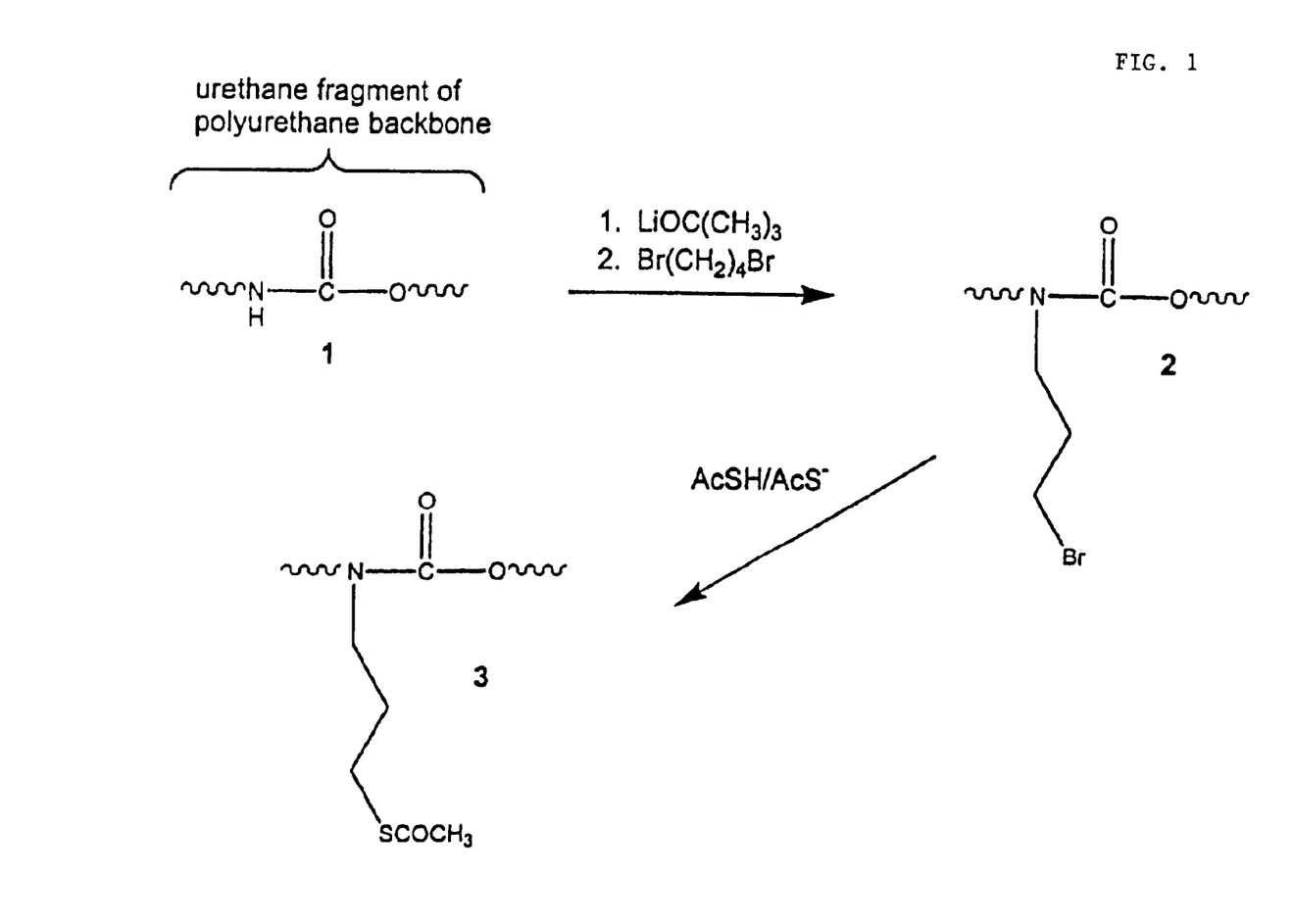
FIG. 1 depicts a synthesis of a polyurethane having a pendant protected thiol group. A urethane amino nitrogen in a polyurethane schematically represented herein as 1 is bromoalkylated to obtain a bromobutyl derivative 2, in which the bromo substituent is subsequently substituted by thiolacetate to obtain polyurethane 3 having a pendant protected thiol group.

Next, the pendant leaving groups are used for further derivatization with latent thiol groups (e.g., acetylthio groups, as shown in FIG. 1) as described above.

Figure 3:
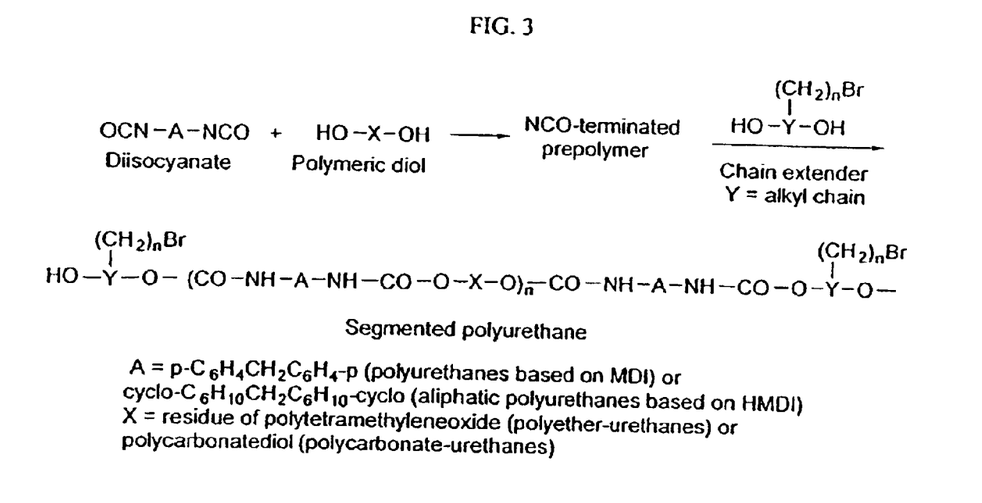
FIG. 3 depicts a synthesis of a polyurethane having a pendant protected thiol group using chain extenders which are pre-modified with reactive bromoalkyl groups. Polyurethane precursors terminated with isocyanate groups are reacted with bromoalkyl-containing diols as chain extenders. Next, the pendant bromoalkyl groups can be used for further derivatization with latent thiol groups (e.g., acetylthio groups, as described in FIG. 1) to obtain polyurethane 3 having a pendant protected thiol group.
Figure 4:
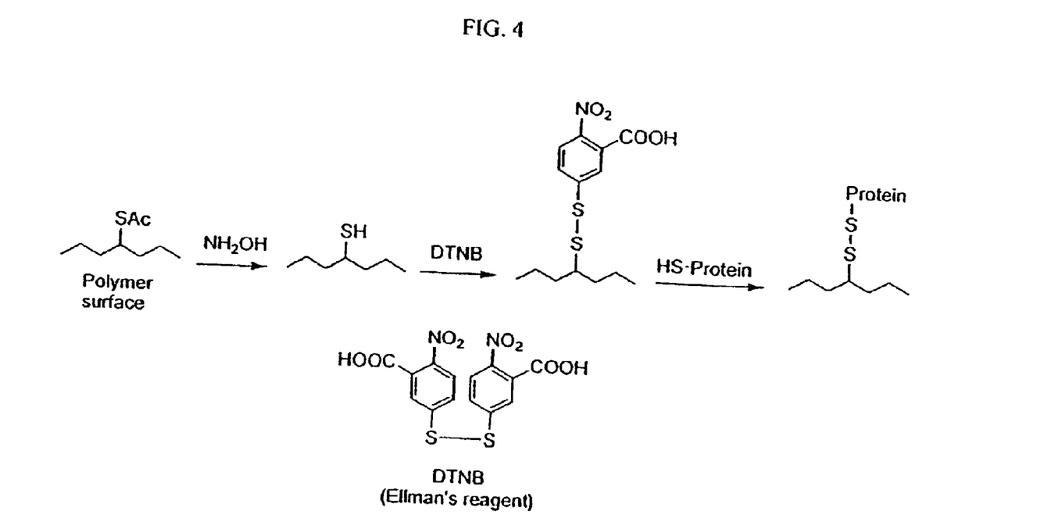
FIGS. 4 and 5 illustrate the use of polyurethane having a pendant protected thiol group for covalent immobilizations of various proteins, wherein in FIG. 4, the proteins are thiol-containing proteins and in FIG. 5, the proteins are succinimidyl 3-(2-pyridyldithio)propionate (SPDP)-treated proteins.
Figure 5:
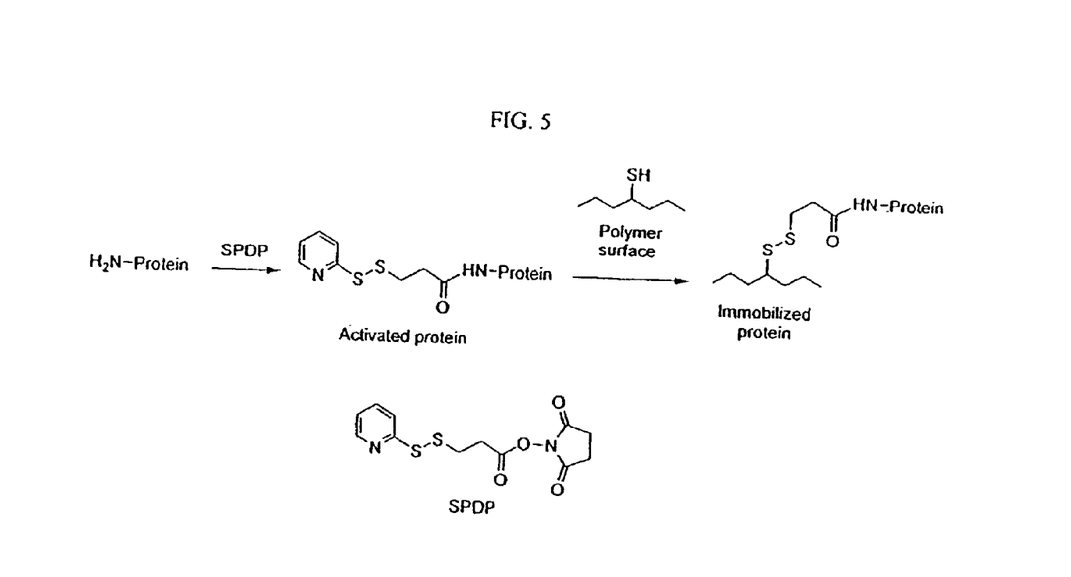

An example of synthesis of a polyurethane having pendant protected thiol groups using chain extenders which are first pre-modified with reactive bromoalkyl groups is shown in FIG. 3 and then further derivatized with latent thiol groups is described in Example 7 below. The resulting polyurethane will have thiol substituents pendant from carbon atoms of the polyurethane in place of leaving groups.

Thiol substituents can be then deprotected as described above.

Further, the polyurethanes of the invention can be assayed to quantify a concentration of pending thiol substituents by a method disclosed in copending U.S. patent application entitled METHOD OF DETERMINING SURFACE BINDING CAPACITY by the inventors filed on even date herewith. The assay is also described in Examples 5 and 6 below.

Inventors discovered that a fluorescent moiety can be used to quantify a number of reactive moieties attached to a surface and consequently ascertain a number of biomolecules capable of binding to the surface via reactive moieties by measuring a signal emitted by the fluorescent moiety.

In the method of the invention, the fluorescent moiety is attached to the surface containing reactive moieties through a cleavable bond, preferably a disulfide bond or an aromatic azo group. The fluorescent moiety is preferably introduced by either a thiol-containing or thiol-reactive fluorophore.

The cleavable bonds are then cleaved to liberate the fluorescent moiety by methods known in the art, for example by using reducing agents.

Then, the liberated fluorescent moiety is detected using common instrumentation, such as a fluorimeter. Quantitative determination of the surface density of reactive moieties can be obtained by comparing the output signal for a surface on which the reactive moieties were not transformed into thiol or thiol-reactive groups (i.e., controls) to the output signal for a surface from which the fluorescent moiety was liberated.

A typical average difference in the concentrations of fluorophore, for example, dansyl-L-cysteine, between treated surfaces and the controls was about 0.4 $\mu$M, which corresponds to about 0.1 nmol/cm$^2$ of thiol-reactive groups on the surface. A linear correlation between the concentration of the fluorophore and the fluorescence intensity was found in the working range of $10^{-8}$–$10^{-6}$M. Calibration curves were made for each set of the fluorescence measurements.

In the experiments described below, the following materials, procedures and apparatuses were used:

A Bruker Advance DMX 400 spectrometer was used for recording the NMR spectra reported herein. Medical grade polyether-urethane Tecothane TT1074A was obtained as pellets from Thermedics Inc. (Woburn, Mass.) and used without any purification. This polymer, represented generally as 1 in FIG. 1, is based on 4,4'-methylenebis(phenyl isocyanate) (MDI), polytetramethylene ether glycol (PTMEG), and 1,4-butanediol as a chain extender.

An analytical sample of the polyurethane was additionally purified by dissolution in dimethyl formamide (DMF), filtration, precipitation with a large volume of cold (−60° C.) methanol, washing with copious amounts of methanol then water, and vacuum-drying. $^1$H NMR (DMF-d$_7$, the intensities are given in arbitrary units) δ 1.51–1.76 (m, 1833H, CH$_2$CH$_2$ in the middle of tetramethylene bridges), 3.35–3.45 (m, 1620H, ether OCH$_2$), 3.87 (br. s, 105H, ArCH$_2$Ar), 4.10–4.17 (m, 211H, urethane OCH$_2$), 7.18 (m close to d, J=8 Hz, 215H, aromatic H, most likely in m-position to NH), 7.51 (br. m close to d, J=8 Hz, 212H, aromatic H, most likely in o-position to NH), 9.49 and 9.52 (two close br. s, total 100H, urethane NH). As calculated from the relative intensities of the aromatic protons and different types of CH$_2$ groups, the polyurethane contains 2.4 mmol/g of urethane groups.

EXAMPLES

The invention will be illustrated in more detail with reference to the following Examples, but it should be understood that the present invention is not deemed to be limited thereto.

Example 1

Preparing Polyurethane With Pendant 4-Bromobutyl Substituents

This example demonstrates a method of derivatizing polyurethane by using a multifunctional linking reagent.

The polyurethane as described above (15.8 g, containing ca. 38 mmol of urethane NH groups) was soaked in toluene (150 ml) for 60 hours. After removal of the excess solvent, the swollen polymer was dried in vacuo at 40° C. and dissolved in dry N,N-dimethylacetamide (DMAc) (300 ml) under a flow of dry argon.

Freshly distilled 1,4-dibromobutane (15 ml, 126 mmol) was added, the solution was cooled to −6° C., and a 1.0 M solution of lithium tert-butoxide in hexanes (Sigma-Aldrich, 7.6 ml, 7.6 mmol) diluted with dry DMAc (20 ml) was added over a 10-minute period with vigorous stirring at −5 to −6° C. The resultant mixture was stirred at −1° to 1° C. for 1 hour with continued argon protection and then acidified with acetic acid (6.5 ml).

The reaction solution was poured into a large volume (1200 ml) of cold (−55° C.) methanol, the resulting coagulate of polymer was separated, thoroughly washed with methanol followed by 2-propanol, and dried in vacuo (0.5 mm Hg) at room temperature.

The crude polymer was redissolved in DMF (275 ml), the solution was filtered, and the polymer was precipitated with cold methanol, washed with large volumes of methanol and water, stirred for 16 hours with a large amount of water at 4° C. and dried in vacuo (0.04 mm Hg) at room temperature to yield 15.64 g of the polyurethane derivative represented generally as 2 in FIG. 1. $^1$H NMR spectral analysis of 2 showed that the concentration of bromobutyl groups was 0.45 mmol per gram of 2.

Example 2

Preparation of a Polyurethane having Pendant Acetylthiobutyl Substituents

This example demonstrates the preparation and thermal stability of a polyurethane having pendant protected thiol groups.

Polyurethane 2 (15.5 g, containing ca. 7.1 mmol of pendant bromobutyl groups) as prepared in Example 1 was dissolved in dry DMAc (220 ml) under a flow of argon, and the solution was cooled to −8° C. Freshly vacuum-distilled (at 115 mm Hg) thiolacetic acid (5.72 ml, 80 mmol), together with a freshly prepared 0.25M DMAc-solution of tetrabutylammonium tetraborate $(Bu_4N)_2B_4O_7$ (80 ml, 20 mmol), was introduced. The temperature was not allowed to exceed 0° C.

The mixture was stirred at −1° to 1° C. for 1 hour with continued Ar protection and then poured into a large volume (1400 ml) of cold methanol (−60° C.). The resulting coagulate of polymer was separated, washed and dried as described in Example 1.

The crude polymer was redissolved in DMF (300 ml), filtered, precipitated with cold methanol, washed with large volumes of methanol and water, stirred for 4 hours with a large amount of water at room temperature and dried at 0.04 mm Hg to yield 14.43 g of the polyurethane represented generally as 3 in FIG. 1. $^1$H NMR spectral analysis of 3 (FIG. 1) showed that the polyurethane contained 0.45 mmol of acetylthio groups per gram of polyurethane and that it contained no unreacted bromobutyl groups.

The acetylthio-modified polyurethane 3 is similar to starting polyurethane 1 in both visual appearance and propensity for water absorption. A sample of polyurethane 3 was heated in vacuo at 209°–214° C., which is the highest temperature recommended by the manufacturer for the thermoprocessing of polyurethane 1. After 5 minutes, polyurethane 3 exhibited no visual changes and no spectral changes (as determined by $^1$H NMR) relative to a sample of polyurethane 3 that was not heated.

Example 3

Formation of Films Prepared from Polyurethane having Pendant Acetylthiobutyl Substituents This example demonstrates the preparation of surfaces in the form of films of the derivatized polyurethane.

Films of the polyurethane described in Example 2 were cast on a Teflon-coated surface using ca. 6% filtered solutions in freshly distilled THF (free of peroxides) in air at room temperature. The cast films were dried in a flow of air for 2–3 days, thoroughly washed with water, and then air-dried. The films exhibited an average thickness of about 0.2 mm.

Example 4

Preparation of Polyurethane having Pendant Butylthiol Substituents

This example demonstrates the deprotection of protected thiol groups to obtain a polyurethane having pendant thiol groups.

The polyurethane films of Example 3 were cut into rectangles (1.3×0.8 cm, total surface area ca. 2 cm$^2$). The films were soaked for 1.5 h in a deoxygenated aqueous solution of hydroxylamine hydrochloride (0.6M), NaOH (0.51M), ethylenediaminetetraacetic acid (EDTA; free acid, 0.3 mg/ml), $Na_2HPO_4$ (52 mM) and sodium dodecyl sulfate (0.1 mg/ml) at 20°–22° C. under a blanket of Ar.

The films were removed from the hydroxylamine solution and rinsed briefly with a 2 mM solution of EDTA disodium salt. The resulant polyurethane, represented generally as 4 in FIG. 2, has pendant thiol groups, the concentration of which was determined in the assay method exemplified below.

Example 5

Preparation of Dansyl-L-Cysteine

This example demonstrates the synthesis of a thiol-reactive fluorophore.

Didansyl-L-cystine (Sigma-Aldrich, 95% pure, 201 mg, 0.28 mmol) was dissolved in methanol (5.4 ml) under Ar, and treated with a solution of tris(2-carboxyethyl)phosphine (TCEP) hydrochloride (Pierce, 107 mg, 0.37 mmol) and NaHCO3 (81 mg, 0.96 mmol) in water (1.1 ml). The resultant mixture was stirred at 20–22° C. for 5 minutes, diluted with 2-propanol (10 ml), and the solvents were quickly removed in vacuo at 20°–25° C. It was found that longer reaction times and delays in the removal of solvents caused formation of a non-separable by-product.

The residue was extracted with $CHCl_3$ (total ca. 15 ml), and the solution was filtered through a layer of cellulose powder. After removal of $CHCl_3$, the residue (ca. 250 mg) was purified by flash-chromatography on a small amount of silica gel in $CHCl_3$—MeOH (100:0 then 95:5 by volume). It was important to finish the chromatography in less than 0.5 hour. Otherwise, a significant loss of dansyl-L-cysteine occurs, most likely due to its oxidation promoted by silica gel.

The purified product, which was a syrup after the removal of solvents, was dissolved in EtOAc (2.5 ml), diluted with n-heptane (4 ml) and slowly dried in vacuo at 20°–23° C., resulting in the solidification of the product. The residual solid powder was further dried at 0.1 mm Hg for 1 hour to yield 152 mg (75%). Dansyl-L-cysteine was characterized by TLC (silica gel, CHCl3—MeOH—AcOH, 95:5:2): Rf ca. 0.4; and $^1$H NMR (CDCl3) δ 1.36 (br., 1H, SH), 2.69 and 2.79 (two br. d, J=14 Hz, 1H and 1H, diastereotopic CH$_2$), 2.91 (s, 6H, CH$_3$), 4.17 (m, 1H, CH), 5.89 (br. d, J=7 Hz, 1H, NH), 7.24 (d, J=7 Hz, 1H, Ar—H), 7.50 (dd, J=8, 7 Hz, 1H, Ar—H), 7.60 (m close to t, J=8 Hz, 1H, Ar—H), 8.24 (dd, J=7, 1 Hz, 1H, Ar—H), 8.35 (d, J=9 Hz, 1H, Ar—H), 8.50 (d, J=9 Hz, Ar—H).

Example 6

Determination of Surface Binding Capacity of Polyurethane having Pendant Butylthiol Substituents This example demonstrates the quantification of thiol groups that are presented by a surface of a polyurethane containing pendant thiol substituents.

The polyurethane films of Example 4 were treated for 1 hour at 20°–22° C. with a solution (pH=7) of with 5,5'-dithiobis(2-nitrobenzoic acid) (DTNB; Sigma-Aldrich, 149 mg), KHCO$_3$ (68 mg), water (1.6 ml) and K$_2$HPO$_4$ (0.18 mmol) to provide a polyurethane with pendant disulfide substituents (represented generally as 5 in FIG. 2). Untreated films (i.e., those of Example 4) served as controls.

Figure 2:
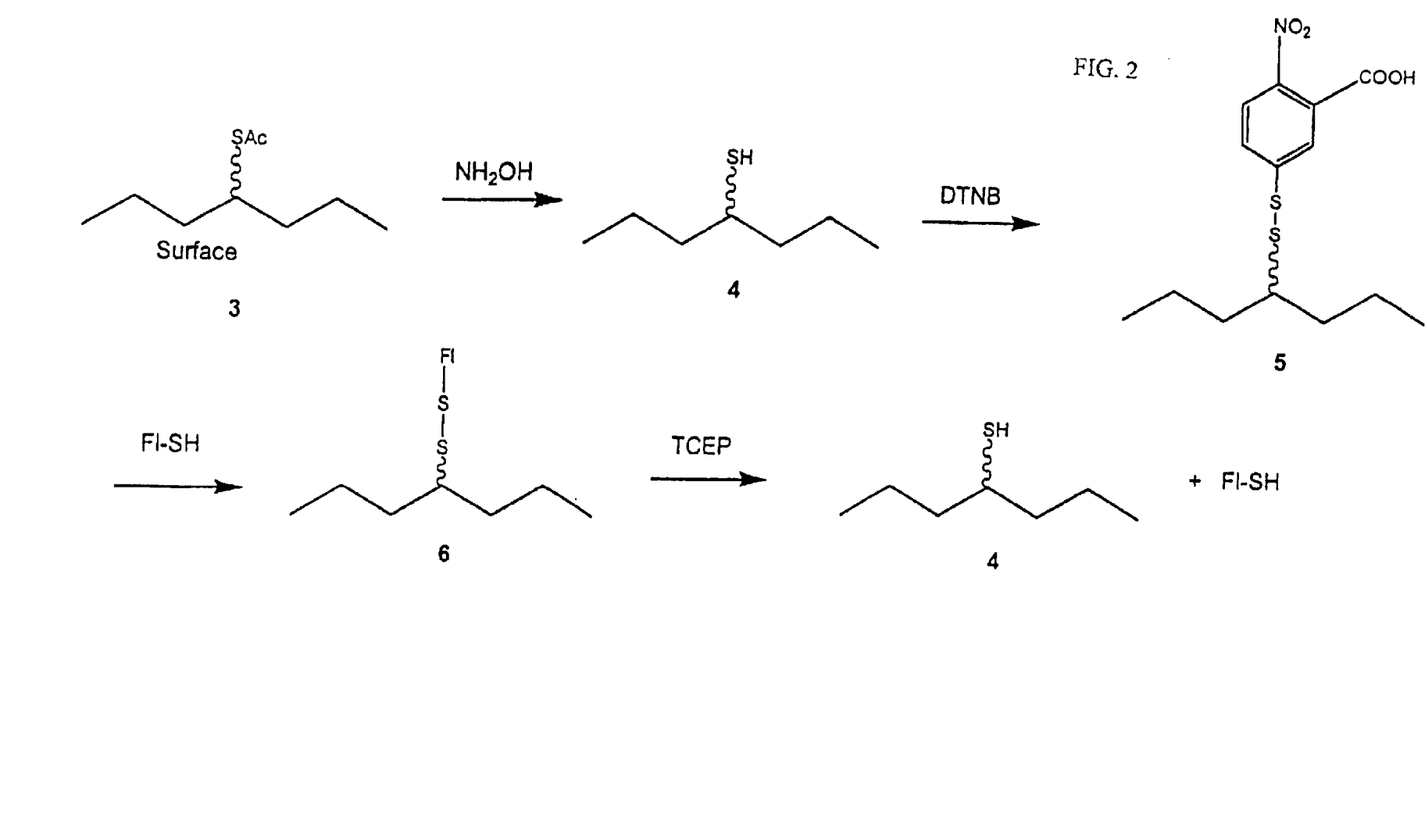

After washing with 0.1M phosphate buffer (pH=7), the films were exposed to a solution of dansyl-L-cysteine (21 mg) of Example 5 (represented generally as Fl-SH in FIG. 2), Na$_2$HPO$_4$ (0.05 mmol) and NaH$_2$PO$_4$ (0.16 mmol) in water (10 ml) for 20 minutes to provide a polyurethane with pendant disulfide substituents (represented generally as 6 in FIG. 2). To remove the unbound dansyl-L-cysteine, the films were stirred with large volumes of a mixture containing Na$_2$HPO$_4$ (6 mM), NaH$_2$PO$_4$ (6 mM), sodium dodecyl sulfate (0.2 mg/ml) and N-ethylmaleimide (Sigma-Aldrich, 0.24 mg/ml) for 5 days at 4° C.

Finally, the films were individually incubated with stirring in 0.5 ml of methanolic solution containing TCEP hydrochloride (5 mg/ml) and NaOAc (2.9 mg/ml) for 20 minutes at 20°14 22° C. to furnish polyurethane 3 and liberate dansyl-L-cysteine (Fl-SH; FIG. 2). The concentrations of released dansyl-L-cysteine (Fl-SH) were determined using a Victor² fluorometer, model 1420 (Wallac, Finland) with a set of filters providing excitation at 355 nm and emission at 535 nm.

A typical average difference in the concentrations of dansyl-L-cysteine between the DTNB-treated films and the controls was 0.4 μM, which corresponds to 0.1 nmol/cm² of thiol-reactive groups on the surface of the polyurethane films. A linear correlation between the concentration of dansyl-L-cysteine and the fluorescence intensity was found in the working range of $10^{-8}$–$10^{-6}$ M. Calibration curves were made for each set of the fluorescence measurements.

Example 7

Synthesis of Polyurethanes having a Pendant Protected Thiol Groups using Chain Extenders As shown in FIG. 3, polyurethane precursors terminated with isocyanate groups are reacted with bromoalkyl-containing diols as chain extenders. In the reaction, A is a polyurethane precursor based on methylene diphenyl diisocyanate (MDI) or an aliphatic polyurethane based on HMDI, X is a residue of polytetramethuleneoxide (polyether-urethanes) or polycarbonatediol (polycarbonate-urethanes), and Y is an alkyl chain. Preferably, Y is a butyl. Conditions for such reaction can be any suitable conditions know in the art for making substituted polymers from blocks using chain extenders.

Next, the pendant bromoalkyl groups can be used for further derivatization with latent thiol groups (e.g., acetylthio groups, as shown in FIG. 1) as described in Example 2 to obtain polyurethane 3 having a pendant protected thiol group.

While the invention has been described in detail and with reference to specific examples thereof, it will be apparent to one skilled in the art that various changes and modifications can be made therein without departing from the spirit and scope thereof.

What is claimed is:

1. A polyurethane comprising a thiol substituent pendant from at least one nitrogen and/or at least one carbon atom of the polyurethane, wherein the thiol substituent comprises a sulfur atom and a removable fragment connected to the sulfur atom provided that when the thiol substituent is pending from the at least one carbon atom, the thiol substituent does not include a SH group.

2. The polyurethane of claim 1, wherein the thiol substituent has a formula:

wherein n is an integer from 1 to 3; $R_L$ is an (n+1)-valent organic radical comprising at least one carbon atom; and $R^1$ is the removable fragment which is a member selected from the group consisting of $C(O)R^3$, and $SR^4$, wherein $R^3$ is a member selected from the group consisting of $C_1$ to $C_6$ alkyl and $R^4$ is a heterocyclic group or an electron deficient aromatic group.

3. The polyurethane of claim 2, wherein $R_L$ is a bivalent organic radical selected from the group consisting of $C_1$ to $C_{18}$ alkylene, $C_1$ to $C_{18}$ alkyleneamino, $C_1$ to $C_{18}$ alkyleneoxy, $C_1$ to $C_{18}$ haloalkylene, $C_2$ to $C_{18}$ alkenylene, $C_6$ to $C_{18}$ arylene, a modified $C_2$ to $C_{18}$ alkenylene having at least one carbon substituted by a halogen group, $C_2$ to $C_{18}$ alkenylene having one or more O, S, or N atoms incorporated into an alkenylene chain, a bivalent heterocyclic radical, and mixtures thereof.

4. The polyurethane of claim 3, wherein $R_L$ is $C_1$ to $C_6$ alkylene.

5. The polyurethane of claim 4, wherein $R_L$ is butylene.

6. The polyurethane of claim 3, wherein the bivalent heterocyclic radical is a member selected from the group consisting of thiazoline, thiazolidone, imidazole, imidazoline, thiazole, tetrazole, thiadiazole, imidazole, pyridine, and morpholine.

7. The polyurethane of claim 6, wherein the bivalent heterocyclic radical is pyridine.

8. The polyurethane of claim 2, wherein $R^1$ is $SR^4$.

9. The polyurethane of claim 2, wherein $R^4$ is 2-pyridyl.

10. The polyurethane of claim 2, wherein $R^4$ is 3-carboxy-4-nitrophenyl.

11. The polyurethane of claim 1, wherein the thiol substituent is pendant from about 0.5 to 50% of urethane nitrogen atoms.

12. The polyurethane of claim 1, wherein the thiol substituent is pendant from about 0.5 to about 50% of carbon atoms.

13. The polyurethane of claim 1, wherein the thiol substituent is pendant from 1 to 20% of urethane nitrogen and/or carbon atoms.

14. The polyurethane of claim 1, wherein the thiol substituent is pendant from 5 to 10% of urethane nitrogen and/or carbon atoms.

15. The polyurethane of claim 1, wherein the polyurethane comprises at least about 10 micromoles of the thiol substituent per gram of the polyurethane.

16. The polyurethane of claim 1, wherein the polyurethane has at least two different thiol substituents pendant from urethane nitrogen and/or carbon atoms.

17. The polyurethane of claim 1, wherein the thiol substituent is an acetylthio group.

18. The polyurethane of claim 1, wherein the thiol substituent is a 3-carboxy-4-nitrophenyldithio group.

19. A process for preparing the polyurethane of claim 1, the process comprising:
providing a polyurethane comprising a urethane amino moiety;
providing a multifunctional linker reagent of a formula:

wherein n is an integer from 1 to 3, FG is a functional group selected from the group consisting of a halogen, a carboxyl group, a sulfonate ester, and an epoxy group, LG is a leaving group selected from the group consisting of a halogen, a carboxyl group, a sulfonate ester, and an epoxy group, and $R_L$ is an (n+1)-valent organic radical comprising at least one carbon atom;
providing a protected thiol-containing reagent of a formula R—C(O)SH, or a salt thereof, wherein R is a $C_1$ to $C_6$ alkyl group;
reacting the multifunctional linker reagent with the urethane amino moiety to form a polyurethane substituted with at least one substituent group of a formula reacting the polyurethane substituted with at least one substituent group with a protected thiol-containing reagent to form the polyurethane comprising the thiol substituent pendant from the at least one nitrogen and/or the at least one carbon atom.

20. The process of claim 19, wherein $R_L$ is a bivalent organic radical selected from the group consisting of $C_1$ to $C_{18}$ alkylene, $C_1$ to $C_{18}$ alkyleneamino, $C_1$ to $C_{18}$ alkyleneoxy, $C_1$ to $C_{18}$ haloalkylene, $C_2$ to $C_{18}$ alkenylene, $C_6$ to $C_{18}$ arylene, a modified $C_2$ to $C_{18}$ alkenylene having at least one carbon substituted by a halogen group, $C_2$ to $C_{18}$ alkenylene having one or more O, S, or N atoms incorporated into an alkenylene chain, a bivalent heterocyclic radical, and mixtures thereof.

21. The process of claim 20, wherein $R_L$ is a member selected from the group consisting of $C_1$ to $C_6$ alkylene.

22. The process of claim 20, wherein $R_L$ is butylene, FG is a bromo group, LG is a bromo group and n is 1.

23. The process of claim 19, wherein LG is a bromo group.

24. The process of claim 19, wherein the sulfonate ester is a member selected from the group consisting of mesylate, triflate, and tosylate.

25. The process of claim 19, the sulfonate ester is a member selected from the group consisting of a ω-bromoalkyl mesylate, a ω-bromoalkyl triflate, and a ω-bromoalkyl tosylate.

26. The process of claim 19, wherein the multifunctional linker reagent is a member selected from the group consisting of a dibromoalkyl compound, a bromo-carboxyalkyl compound, and a bromo-epoxyalkyl compound.

27. The process of claim 26, wherein the dibromoalkyl compound is a 1,ω-dibromoalkyl compound or a substituted 1,ω-dibromoalkyl compound.

28. The process of claim 27, wherein the dibromoalkyl compound is a $C_2$–$C_6$1,ω-dibromoalkyl compound.

29. The process of claim 27, wherein the dibromoalkyl compound is 1,6-dibromohexane or 1,4-dibromobutane.

30. The process of claim 26, wherein the bromo-carboxyalkyl compound is a ω-bromocarboxylic acid or a substituted ω-bromocarboxylic acid.

31. The process of claim 26, wherein the bromo-epoxyalkyl compound is epibromohydrin.

32. The process of claim 19, wherein the process is conducted in a presence of an aprotic solvent.

33. The process of claim 32, wherein the aprotic solvent is a member selected from the group consisting of N,N-dimethylacetamide, N,N-dimethyl formamide, 1-methyl-2-pyrrolidinone, tetrahydrofuran, dioxane, and dimethyl sulfoxide.

34. The process of claim 19, wherein the process is conducted in a presence of a base soluble in the aprotic solvent.

35. The process of claim 34, wherein the base is a member selected from the group consisting of sodium hydride, lithium diisopropylamide, and sodium.

36. The process of claim 34, wherein the base is potassium tert-butoxide, dimsyl sodium, lithium hydride, sodium amide, lithium N,N-dialkylamide, or lithium N,N-dicyclohexylamide.

37. The process of claim 34, wherein the base is lithium tert-butoxide.

38. The process of claim 36, wherein the multifunctional linker reagent is 1,6-dibromohexane, and the base is lithium diisopropylamide.

39. The process of claim 27, wherein the multifunctional linker reagent is 1,4-dibromobutane.

40. The process of claim 19, wherein the protected thiol-containing reagent is thiolacetic acid.

41. The process of claim 19, wherein the protected thiol-containing reagent is tetrabutylammonium thioacetate.

42. The process of claim 19, further comprising reacting the protected thiol group with a deprotecting reagent to remove an R—C(O)—fragment from the thiol substituent to obtain the polyurethane.

43. The process of claim 42, wherein the deprotecting reagent is a member selected from the group consisting of ammonia, primary aliphatic amines, aqueous solutions of alkali metal hydroxides, carbonates, tri-substituted phosphates, hydroxylamine, and hydrazine.

44. A process of producing a molded product, said process comprising:
provifing the polyurethane of claim 1, wherein the thiol substituent is protected;
molding the polyurethane to form an article; and
deprotecting the thiol substituent of the article to provide the molded product.

45. The process of claim 44, further comprising reacting the thiol substituent of the molded product with a biomolecule.

46. A molded product produced by the process of claim 44.

47. The molded product of claim 46, wherein the molded product is an implantable device.

* * * * *